United States Patent [19]

Przybilla et al.

[11] Patent Number: 5,326,840
[45] Date of Patent: Jul. 5, 1994

[54] RADIATION-SENSITIVE MIXTURE CONTAINING NOVEL POLYMERS EMBODYING UNITS COMPOSED OF AMIDES OF α, β-UNSATURATED CARBOXYLIC ACIDS AS BINDERS

[75] Inventors: Klaus-Juergen Przybilla, Frankfurt am Main; Georg Pawlowski, Wiesbaden; Horst Roeschert, Ober-Hilbersheim, all of Fed. Rep. of Germany

[73] Assignee: Hoechst Aktiengesellschaft, Frankfurt am Main, Fed. Rep. of Germany

[21] Appl. No.: 895,666

[22] Filed: Jun. 9, 1992

[30] Foreign Application Priority Data

Jun. 19, 1991 [DE] Fed. Rep. of Germany ....... 4120172

[51] Int. Cl.⁵ .................... C08F 20/60; C08F 24/00; C08F 30/08
[52] U.S. Cl. ................................. 526/262; 526/266; 526/270; 526/279; 526/304; 526/292.9; 526/292.95; 430/906; 430/910; 430/270
[58] Field of Search .................. 526/304, 298, 292.95, 526/292.2, 262, 266, 270, 279, 292.9; 430/906, 910, 270

[56] References Cited

U.S. PATENT DOCUMENTS

| | | | |
|---|---|---|---|
| 4,491,628 | 1/1985 | Ito et al. | 430/176 |
| 4,689,288 | 8/1987 | Buiguez et al. | 430/270 |
| 4,770,977 | 9/1988 | Buiguez et al. | 430/323 |
| 4,822,719 | 4/1989 | Schneller et al. | 430/270 |
| 4,908,381 | 3/1990 | Greenwald et al. | 514/460 |
| 4,946,761 | 8/1990 | Maemoto | 430/270 |
| 5,120,629 | 6/1992 | Bauer et al. | 430/70 |
| 5,130,392 | 7/1992 | Schwalm et al. | 526/288 |

FOREIGN PATENT DOCUMENTS 3825738 3/1989 Fed. Rep. of Germany .
1-227143 12/1989 Japan .

OTHER PUBLICATIONS

J. March, "Advanced Organic Chemistry," 3rd Ed., McGraw–Hill, New York, (1985), pp. 684–686.
T. W. Greene, "Protective Groups in Organic Chemistry," Wiley, New York, 1981, pp. 21–24, 94–98.
Crivello *Org. Coatings and Appl. Polym. Sci.* 48:65–69, (1985) Applications of Photoinitiated Cationic Polymerization Toward the Development of New Photoresists.
Ito *J. of Poly. Sci., Part A, Polym. Chem. Ed.*, 24:2971–80, (1986) Solid-State Thermolysis of Poly(p-t-Butoxycarbonyloxystyrene) Catalyzed by Polymeric Phenol: Effect of Phase Separation.

*Primary Examiner*—Mark Nagumo
*Attorney, Agent, or Firm*—Foley & Lardner

[57] ABSTRACT

A radiation-sensitive mixture is disclosed that contains a polymeric binder having acid-cleavable side groups and a compound which forms a strong acid on irradiation. Novel amides of α,β-unsaturated carboxylic acids with which the polymers used as binders are synthesized are also disclosed. A positive- or negative-working radiation-sensitive recording material comprising a base and a layer of the radiation-sensitive mixture according to the invention is also disclosed.

18 Claims, No Drawings

RADIATION-SENSITIVE MIXTURE CONTAINING NOVEL POLYMERS EMBODYING UNITS COMPOSED OF AMIDES OF α,β-UNSATURATED CARBOXYLIC ACIDS AS BINDERS

BACKGROUND OF THE INVENTION

The present invention relates to a radiation-sensitive mixture containing a polymeric binder having acid-cleavable side groups and a compound that forms a strong acid on irradiation. It also relates to novel amides of α,β-unsaturated carboxylic acids with which the polymers used as binders are synthesized.

Radiation-sensitive mixtures are known per se. Commercially-available, positive-working mixtures are especially used as resist material. These contain, in addition to o-quinone diazide, a binder that is soluble in aqueous-alkaline solution, such as poly(4-hydroxystyrene) or a novolak. The sensitivity of these systems to radiation, particularly short-wave radiation, is sometimes unsatisfactory. As a result of the high intrinsic absorption in the UV-2 range (220-300 nm), novolaks are unsuitable as binders in a single-layer resist material for deep-UV lithography (220-330 nm). Poly(hydroxystyrene) has, on the other hand, more favorable absorption properties in the UV range. It also has a higher thermal stability. However, this polymer can only be obtained by elaborate multistage syntheses. Its lithographic properties are also unsatisfactory in both 3-component systems and 2-component systems because of a poor hydrophilic/hydrophobic balance. There is therefore a need for binders for high-resolution, high-sensitivity resist materials that have good etch resistance, good transparency and high thermal stability for UV-2 lithography and that can be developed in aqueous-alkaline solutions.

It is also known to increase the radiation sensitivity of radiation-sensitive mixtures by adding a compound that, on exposure to radiation, releases an acid that then catalyzes secondary reactions. Such compounds are, for example, diazonium, phosphonium, sulfonium and iodonium salts, nitrobenzyl esters, phenolic methanesulfonates and diazo and halogen compounds. The use of the onium salts as photochemical acid formers in resist materials is disclosed, for example, by U.S. Pat. No.4,491,628. A review of the use of onium salts in resist materials is given by Crivello in Org. Coatings and Appl Polym. Sci., 48: 65-69 (1985).

Radiation-sensitive mixtures of polymers containing acid-labile side groups and photochemical acid formers are disclosed by U.S. Pat. No.4,491,628 and FR 2,570,844 (≈ U.S. Pat. Nos.4,689,288 and 4,770,977). Only polymers of p-substituted styrene or α-alkylstyrene are disclosed in the two publications mentioned. Tert-butoxycarbonyloxy and trialkylsilanyloxy groups are identified as acidlabile p-substituents. These polymeric binders are hydrophobic and become soluble in alkali only after exposure.

Copolymers containing acid-labile groups that are bound via a phenolic oxygen atom, for example, copolymers of p-hydroxystyrene and tertbutoxycarbonyloxystyrene, are disclosed in *J. Poly. Sci.*, Part A, Polym. Chem. Ed., Vol. 24: 2971-80 (1986).

SUMMARY OF THE INVENTION

It is therefore an object of the present invention to provide a mixture that is highly radiation-sensitive in the short-wave UV range for preparing relief structures, which mixture can be developed with aqueous-alkaline solutions.

These and other objects according to the invention are provided by a compound of the formula II

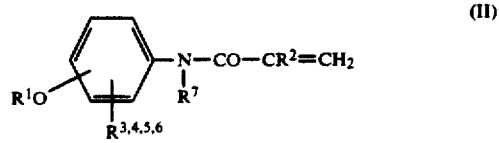

where
R$^1$ is an acid-cleavable group,
R$^2$ is (C$_1$-C$_4$) alkyl, halogen (C$_1$-C$_4$) alkyl or hydrogen,
R$^{3,4,5,6}$ are, independently of one another, an optionally halogen-substituted aliphatic, araliphatic or aromatic radical containing 1 to 20 carbon atoms, a halogen atom or hydrogen, and
R$^7$ is (C$_1$-C$_4$) alkyl or hydrogen.

A radiation-sensitive mixture comprises a combination of a polymeric binder derived from the foregoing monomer having acid-cleavable side groups and a compound which forms a strong acid on irradiation. A process for producing relief structures comprises the steps of applying a photoresist layer containing this radiation-sensitive mixture to a substrate and drying it to produce a layer having a thickness of about 0.1 to 5 μm, imagewise exposing the layer, optionally heating the layer to temperatures of up to about 150° C. and developing the layer to produce an image. To produce a positive image the layer is developed with an aqueous-alkaline solution. To produce a negative image the layer is developed with an organic solvent.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

According to the invention, a radiation-sensitive mixture contains a polymeric binder having acid-cleavable side groups and a compound that forms a strong acid on irradiation. The radiation-sensitive mixture contains novel polymers embodying units of the formula (I)

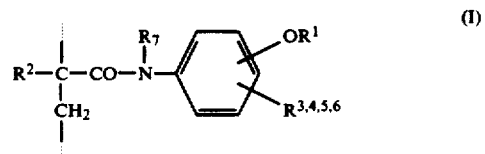

where
R$^1$ is an acid-cleavable group, and
R$^2$ is (C$_1$-C$_4$) alkyl, halogen (C$_1$-C$_4$) alkyl or hydrogen,
R$^{3,4,5,6}$ are, independently of one another, an optionally halogen-substituted aliphatic, araliphatic or aromatic radical containing 1 to 20 carbon atoms, a halogen atom or hydrogen, and is ($C_1$-$C_4$) alkyl or hydrogen.

Compared with the known mixtures containing polystyrene, novolaks or polymers embodying units composed of esters of $\alpha,\beta$-unsaturated carboxylic acids as binders, the polymer and/or the mixture according to the invention has the following advantages:

(a) as a result of the higher nucleophilicity of the amino groups bound to an aromatic ring, the monomeric amides of the $\alpha,\beta$-unsaturated carboxylic acids can be selectively synthesized, (b) the monomeric amides of the $\alpha,\beta$-unsaturated carboxylic acids can be synthesized in water without organic solvent, a considerable process advantage, (c) as a result of the nature of the amide bond and the hydrogen bonds resulting therefrom the polymers have a thermal stability that is substantially higher than that of polymers prepared from corresponding esters, (d) the protected monomers are easily accessible, (e) the unprotected monomers are stable, (f) the protected and the unprotected monomers can be homo- and co-polymerized to produce high molecular polymers, (g) good etch resistance, (h) good hydrophilic/hydrophobic balance, and (i) good adhesion properties.

Polymers embodying units of the formula I can in principle be prepared in two different ways.

On the one hand, so-called "protected" monomers of the formula II

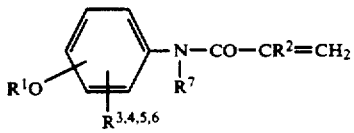

(II)

where $R^1$ to $R^7$ have the meaning specified above, are polymerized either alone or together with other monomers. These monomers are novel and are part of the present invention. Examples of monomers of the formula II are derivatives, formed with acid-labile groups $R^1$ of N-(2-, 3- and 4-hydroxyphenyl)(meth)acrylamide. In particular, benzyl, trialkylsilanyl, tertbutoxycarbonyl, isopropoxycarbonyl, benzyloxycarbonyl, pentyloxycarbonyl, tetrahydropyranyl or tetrahydrofuranyl are suitable as acid-cleavable group $R^1$. Particularly preferred are those monomers in which $R^2$ is hydrogen or methyl and $R^3$, $R^4$, $R^5$ and $R^6$ are all hydrogen. Particularly preferred monomers are N-(4-tert-butoxycarbonyloxyphenyl)(meth)acrylamide, N-(3-tert-butoxycarbonyloxyphenyl)(meth)acrylamide and N-(2-tert-butoxycarbonyloxyphenyl)(meth)acrylamide.

On the other hand, the N-(hydroxyphenyl)(methacryl) amides can be polymerized to form polymers having high molecular weights since they are stable in monomeric form. These polymers can then be derivatized in a subsequent step in order to introduce the groups $R^1$. This procedure is not, however, preferred since the phenolic hydroxy groups in the polymers cannot always be reproducibly derivatized. At the same time, in the case of the two-stage process, it is inevitable that residues of the base used in the derivatization reaction are left behind in the product.

However, 4-hydroxystyrene is not stable in free form. In addition, it can only be prepared in a 4-stage synthesis with poor yields. For this reason, only a protected 4-hydroxystyrene, such as 4-(tert-butoxycarbonyloxy)styrene, can be used as starting material for the polymerization. The latter is prepared from 4-hydroxybenzaldehyde via a Wittig reaction (U.S. Pat. No.4,491,628). As an alternative to this, poly (4-hydroxystyrene) containing suitable protective groups can be reacted. This preparation process has, however, the serious disadvantage that the binder is consequently contaminated with metal ions and with base. The presence of bases is disadvantageous for systems that are photochemically more highly active and a high metal ion contamination is unacceptable for the production of semiconductors. Binders prepared by this process frequently have unreproducible lithographic properties. These disadvantages are not associated with the polymers according to the invention and the radiation-sensitive mixture according to the invention.

The polymeric binders according to the invention may be either homopolymers that contain solely units of the formula I or copolymers and terpolymers. The copolymers and terpolymers preferably contain, in addition to the units of the formula I, units derived from "unprotected" and/or acid-labile protected monomers of the formula II (in these monomers, $R^1$ is hydrogen or a radical which is not acid-cleavable). Units may also occur which are derived from other standard vinyl monomers. In particular, methacrylic acid and esters or amides of (meth)acrylic acid, such as hydroxyethyl methacrylate (HEMA), hydroxypropyl methacrylate, methacrylamide and hydroxyethyl methacrylamide as well as methyl methacrylate and ethyl methacrylate may act as such additional monomers. This makes it possible to modify the adhesive properties of the binder. Mixtures having increased plasma resistance are obtained if silicon-containing monomers are used for the preparation of copolymers or terpolymers. Copolymers with maleimide have an increased solubility in aqueous-alkaline solutions and a higher transparency in the deep-UV range. The same effect is also shown by copolymers with styrene, substituted styrene, with vinyl ethers, vinyl esters, vinylsilane compounds or (meth)acrylates.

The polymers according to the invention contain at least about 10 mol-% of units of the formula I. Their average molecular weight $M_a$ is between about 2,000 and 100,000, preferably between about 5,000 and 40,000, g/mol.

The binder containing acid-cleavable groups is generally contained in the mixture according to the invention in amounts of from about 45 to 98% by weight, preferably about 90 to 98% by weight, based on the total weight of solids in the radiation-sensitive mixture.

The mixture according to the invention also contains a photoactive compound that releases a strong acid on irradiation. The strong acid cleaves off the protective groups present in the binder to increase markedly the solubility of the binder and, consequently, also the mixture in aqueous-alkaline solution. The mixture is particularly sensitive to UV radiation (220–400 nm), electron beams and X-rays and is particularly suitable as resist material. It can also be used to produce printing plates.

Suitable acid formers are all compounds that form a strong acid on irradiation. Examples of particularly suitable acid formers are sulfonium salts of the formula $[(C_6H_5)_3S]^+X$, where X is, in particular, chloride, bromide, perchlorate, hexafluorophosphate, hexafluoroarsenate, hexafluoroantimonate, tetrafluoroborate or a sulfonate, such as methanesulfonate, trifluoromethanesulfonate, tosylate or hexafluoropropanesulfonate. Nitrobenzyl esters, bissulfonyldiazomethanes, pyrogallolsulfonates, 1-sulfonyloxy-2-pyridones and halogen compounds are also suitable. For irradiation with short-wave UV radiation, iodonium, and particularly, sulfonium, salts are preferred. The acid former is present in the mixture in an amount of about 1 to 40% by weight, preferably about 3 to 10% by weight, based on the total weight of solids in the radiation-sensitive mixture.

The radiation-sensitive mixture according to the invention may also contain other standard auxiliaries and additives, such as adhesion promoters, wetting agents, dyes and plasticizers. Optionally, sensitizers can also be added in small amounts in order to sensitize the acid former to radiation in the longer-wave UV up into the visible range. Polycylic aromatics such as pyrene and perylene are preferred for this purpose, but dyes that act as sensitizers may also be used.

The present invention also relates to a recording material having a base and a layer containing the radiation-sensitive mixture according to the invention. A process for producing relief structures or for structuring wafers is also provided.

In order to be able to apply the mixture according to the invention to a base material, it is expediently dissolved in an organic solvent, the solid content generally being in the range between about 5 and 40% by weight. Preferred solvents are aliphatic ketones, ethers and esters, and any desired mixtures thereof. Particularly preferred are alkylene glycol monoalkyl ethers, such as, for example, ethylcellosolve, ethylene glycol monobutyl ether, methylcellosolve and 1-methoxy-2-propanol, alkylene glycol alkyl ether esters, such as, for example, methylcellosolve acetate, ethylcellosolve acetate, propylene glycol methyl ether acetate and propylene glycol ethyl ether acetate, ketones, such as, for example, cyclohexanone, cyclopentanone and butanone, and also acetates, such as butyl acetate, and aromatics, such as toluene and xylene. The choice of the suitable solvent or solvent mixture depends on the choice of the particular phenolic polymers and the photosensitive components.

In the process according to the invention for producing relief patterns, a radiation-sensitive recording layer which is essentially composed of the radiation-sensitive mixture according to the invention is irradiated imagewise with a dose that increases the solubility of the exposed regions in aqueous-alkaline solvents. These irradiated regions can then be selectively removed with the alkaline developer to obtain a positive image.

Development with organic solvents, especially aromatic solvents, such as toluene and anisole is also possible. The unexposed regions have a more lipophilic nature and are therefore removed to produce a negative image.

Depending on the choice of development process, the radiation-sensitive mixture according to the invention functions positively or negatively. It is suitable, in particular, as a photoresist for producing relief structures for semiconductor components.

The photoresist solutions containing the radiation-sensitive mixture according to the invention are generally applied in layers of about 0.1 to 5 μm, preferably about 0.5 to 1.5 μm, to suitable substrates. For example, the solution may be applied to a superficially oxidized silicon wafer by spin coating, dried (for example, at temperatures between about 70° and 130° C.) and then imagewise exposed through a photomask using a suitable light source. Suitable light sources are, in particular, short-wave UV radiation (deep UV) having wavelengths between about 200 and 400 nm. Particularly suitable light sources are excimer lasers.

After the imagewise exposure, development is carried out with standard aqueous-alkaline developer solutions, generally at pHs of between 12 and 14, possibly after a short baking (post-bake) at temperatures of up to about 150° C. During development the exposed areas are washed out. The resolution is in the subsemimicrometer range. The exposure energy required for the radiation-sensitive mixture according to the invention is generally between about 5 and 200 mJ/cm$^2$ for layer thicknesses of about 1 μm.

The developed resist structures are optionally postcured. This is generally done by heating the resist structure on a hot plate to a temperature below the flow temperature and then exposing the entire surface to UV light from a xenon/mercury vapor lamp (range 200 to 250 nm). This postcuring crosslinks the resist structures so that the structures have generally a flow resistance up to temperatures of over 200° C. The postcuring can also be carried out without increasing the temperature by irradiation with UV light. This is particularly so if high-energy radiation is used.

The radiation-sensitive mixture according to the invention is preferably applied in lithographic processes for producing integrated circuits or discrete electrical components. The recording material produced from the mixture is used as a mask in this process for the subsequent processing steps. These include, for example, the etching of the layer base, the implantation of ions in the layer base or the deposition of metals or other materials on the layer base. In addition, the radiation-sensitive mixture according to the invention is also suitable for producing printing plates.

The following examples illustrate the preparation of the monomers, homopolymers and copolymers, and their physical and lithographic characterization. Unless otherwise specified, the parts and percentages specified in the examples are parts by weight (pbw) and percent by weight (wt.-%). N-(Hydroxyphenyl)(meth)acrylamides are prepared by analogy with the process specified in Sololawa et al., *J. Gen. Chem. USSR* (Engl. Transl.), 33: 1466 (1963).

PREPARATION EXAMPLE 1

N-(3-Hydroxyphenyl) methacrylamide

3-Aminophenol (100 g) is suspended in 500 ml of water. Methacrylic anhydride (154 g) is added dropwise at 50° C. When addition is complete, stirring is carried out for a further 2 hours at 70° C. White crystals precipitate from the aqueous reaction solution. The mixture is cooled in an ice bath and the crystal cake is filtered off by suction, washed with water, dried and recrystallized from acetonitrile.

Yield: 90%.

Melting point: 176° C.

PREPARATION EXAMPLE 2

N-(4-tert-Butoxycarbonyloxyphenyl) methacrylamide

K$_2$CO$_3$ (30 g) is added to a solution of 20.0 g (0.112 tool) of N-(4-hydroxyphenyl)methacrylamide in tetrahydrofuran (THF). A solution of 27 g (0.124 tool) of di-tert-butyl pyrocarbonate (di-tert-butyl dicarbonate) in THF is then added at room temperature while stirring. The reaction is complete after a few hours. The reaction mixture is poured onto ice and extracted with ethyl acetate, the organic phase is dried and the solvent is distilled off. A white crystalline product is obtained which is recrystallized from diisopropyl ether.

Yield: 95%.

Melting point: 100° C.

PREPARATION EXAMPLE 3

N-(3-tert-Butoxycarbonyloxyphenyl) methacrylamide $K_2CO_3$ (50 g) is added to a solution of 40.0 g (0.225 mol) of N-(3-hydroxyphenyl)methacrylamide in tetrahydrofuran (THF). A solution of 54.2 g (0.249 mol) of di-tert-butyl pyrocarbonate (di-tert-butyl dicarbonate) in THF is then added dropwise at room temperature while stirring. The reaction is complete after a few hours. The reaction mixture is poured onto ice and extracted with ethyl acetate, the organic phase is dried and the solvent is distilled off. A white crystalline product is obtained which is recrystallized from diisopropyl ether.

Yield: 95%.

Melting point: 102° C.

PREPARATION EXAMPLE 4

N-(2-tert-Butoxycarbonyloxyphenyl) methacrylamide $K_2CO_3$ (30 g) is added to a solution of 20.0 g (0.112 tool) of N-(2-hydroxyphenyl)methacrylamide in tetrahydrofuran (THF). A solution of 27 g (0.124 tool) of di-tert-butyl pyrocarbonate (di-tert-butyl dicarbonate) in THF is then added dropwise at room temperature while stirring. The reaction is complete after a few hours. The reaction mixture is poured onto ice and extracted with ethyl acetate, the organic phase is dried and the solvent is distilled off. A yellowish oil is obtained which decomposes on distillation. The product is used for polymerization without further purification.

Yield: 95%.

PREPARATION EXAMPLES 5 TO 7

Poly[N-(2-hydroxyphenyl) methacrylamide

Poly[N-(3-hydroxyphenyl) methacrylamide

Poly[N-(4-hydroxyphenyl) methacrylamide

Ten g (56 mmol) of the respective monomer is heated under reflux with 0.370 g (2.3 mmol) of azobisisobutyronitrile (AIBN) in 100 ml of distilled THF for 8 hours under nitrogen atmosphere. The polymer is precipitated in petroleum ether and dried in a vacuum drying oven at 50° C.

Yields: 9–10 g.

PREPARATION EXAMPLES 8 TO 10

Poly[N-(2-tert-butoxycarbonyloxyphenyl) methacrylamide

Poly[N-(3-tert-butoxycarbonyloxyphenyl) methacrylamide

Poly[N-(4-tert-butoxycarbonyloxyphenyl) methacrylamide

Fifteen g (54 mmol) of the respective monomer is heated under reflux with 0.355 g (2.1 mmol) of azobisisobutyronitrile (AIBN) in 100 ml of distilled THF for 8 hours under nitrogen atmosphere. The polymer is precipitated in petroleum ether and dried in a vacuum drying oven at 50° C.

Yields: 10–13 g.

Molecular weights: $M_w$: 20,000 g/mol, $M_a$: 12,000 g/mol.

PREPARATION EXAMPLE 11

Copolymers of N-(3-tert-butoxycarbonyloxyphenyl) methacrylamide and N-(3-hydroxyphenyl)methacrylamide are prepared in various monomer ratios under the conditions specified in Example 6. Twenty mol-% of free OH groups are sufficient to achieve good adhesion properties.

The following Application Examples 1 to 4 confirm the suitability of the mixture according to the invention for recording materials in microlithography. The 1-sulfonyloxy-2-pyridones used in these examples and processes for preparing them are described in German Patent Application P 41 12 967.9.

APPLICATION EXAMPLE 1

A solution of a radiation-sensitive mixture is prepared that contains 2.5 pbw of a copolymer of 30% N-(3-hydroxyphenyl) methacrylamide and 70% N-(3-tert-butoxycarbonyloxyphenyl) methacrylamide, 0.075 pbw of 4-methyl-6-styryl-1-trifluoromethanesulfonyloxy-2-pyridone, and 7.5 pbw of propylene glycol monomethyl ether acetate.

An amount of 1.5 ml of this solution is filtered through a filter having a pore diameter of 0.2 μm and applied to a silicone wafer coated with hexamethyldisilazane as adhesion promoter. An approximately 1 μm thick homogeneous layer is produced by rotation at 4,500 rev/min for 45 seconds. The wafer is dried on a hot plate at 100° C. for 60 seconds, then brought into contact with an imagewise structured test mask and irradiated with 365 nm radiation (70 mJ/cm$^2$) using a xenon/mercury vapor lamp with an interference filter interposed. Then the wafer is kept for 1 minute at 80° C. and developed in a 0.27 N aqueous tetramethylammonium hydroxide solution for 180 seconds. Structures of 0.70 μm (line/space) are resolved.

APPLICATION EXAMPLE 2

A solution of a radiation-sensitive mixture is prepared that contains:

2.5 pbw of a copolymer of 30% (2-hydroxyphenyl)methacrylate and 70% N-(3-tert-butoxycarbonyloxyphenyl)methacrylamide, 0.075 pbw of 4-methyl-6-styryl-1-trifluoromethanesulfonyloxy-2-pyridone, and 7.5 pbw of propylene glycol monomethyl ether acetate.

An amount of 1.5 ml of this solution is filtered through a filter having a pore diameter of 0.2 μm and applied to a silicone wafer coated with hexamethyldisilazane as adhesion promoter. An approximately 1 μm thick homogeneous layer is produced by rotation at 4,500 rev/min for 45 seconds. The wafer is dried on a hot plate at 100° C. for 60 seconds, then brought into contact with an imagewise-structured test mask and irradiated with 365 nm radiation (70 mJ/cm$^2$) using a xenon/mercury vapor lamp with an interference filter interposed. Then the wafer is kept for 1 minute at 80° C. and developed with a 0.27 N aqueous tetramethylammonium hydroxide solution for 180 seconds. Structures of 0.70 μm (line/space) are resolved.

APPLICATION EXAMPLE 3

A solution of a radiation-sensitive mixture is prepared that contains:

2.5 pbw of a copolymer of 30% methacrylic acid and 70% N-(3-tert-butoxycarbonyloxyphenyl)methacrylamide, 0.075 pbw of 4-methyl-6-styryl-1-trifluoromethanesulfonyloxy-2-pyridone, and 7.5 pbw of propylene glycol monomethyl ether acetate.

An amount of 1.5 ml of this solution is filtered through a filter having a pore diameter of 0.2 μm and applied to a silicone wafer coated with hexamethyldisilazane as adhesion promoter. An approximately 1 μm thick homogeneous layer is produced by rotation at 4,500 rev/min for 45 seconds. The wafer is dried on a hot plate at 100° C. for 60 seconds, then brought into contact with an imagewise-structured test mask and irradiated with 365 nm radiation (70 mJ/cm$^2$) using a xenon/mercury vapor lamp with an interference filter interposed. Then the wafer is kept for 1 minute at 80° C. and developed with a 0.18 N aqueous tetramethylammonium hydroxide solution for 60 seconds. Structures of 0.70 μm (line/space) are resolved.

APPLICATION EXAMPLE 4

A solution of a radiation-sensitive mixture is prepared from:

2.5 pbw of a copolymer of 30% pyrocatechol monomethacrylate and 70% N-(3-tert-butoxycarbonyloxyphenyl)methacrylamide, 0.075 pbw of 4-methyl-6-styryl-1-trifluoromethanesulfonyloxy-2-pyridone, and 7.5 pbw of propylene glycol monomethyl ether acetate.

Of this solution, 1.5 ml are filtered through a filter having a pore diameter of 0.2 μm and applied to a silicone wafer coated with hexamethyldisilazane as adhesion promoter. An approximately 1 μm thick homogeneous layer is produced by rotation at 4,500 rev/min for 45 seconds. The wafer is dried on a hot plate at 100° C. for 60 seconds then brought into contact with an imagewise-structured test mask and irradiated with 248 nm radiation (70 mJ/cm$^2$) using a xenon/mercury vapor lamp and an interference filter. Then the wafer is kept for 1 minute at 80° C. and developed with anisole for 120 seconds. Structures of 0.70 μm (line/space) are resolved.

What is claimed is:

1. A polymer embodying units of the formula I

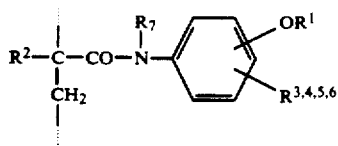

(I)

where
  R$^1$ is an acid-cleavable benzyl, trialkylsilyl, alkoxycarbonyl, tetrahydropyranyl or tetrahydrofuranyl group,
  R$^2$ is (C$_1$–C$_4$) alkyl, halogen (C$_1$–C$_4$) alkyl or hydrogen,
  R$^{3,4,5,6}$ are, independently of one another, an optionally halogen-substituted aliphatic, araliphatic or aromatic radical containing 1 to 20 carbon atoms, a halogen atom or hydrogen, and
  R$^7$ is (C$_1$–C$_4$) alkyl or hydrogen.

2. A polymer as claimed in claim 1, wherein the group R$^1$ is a tert-butoxycarbonyl group.

3. A polymer as claimed in claim 2, which comprises at least 10 mol% of units of formula (I).

4. A polymer as claimed in claim 1, comprising at least 10 mol-% of units of the formula I and, for the remainder, polymerized units of other vinyl monomers.

5. A polymer as claimed in claim 1, which is a homopolymer and contains no further units in addition to the units of the formula I.

6. A polymer as claimed in claim 1, which is a terpolymer that contains, in addition to units of the formula I containing acid-cleavable groups, units of the formula I where R$^1$ is H or a non-acid-cleavable group and units derived from a further polymerizable monomer.

7. A polymer as claimed in claim 1, which is a terpolymer that contains, in addition to units of the formula I containing acid-cleavable groups, units of the formula I where R$^1$ is hydrogen or a non-acid-cleavable group.

8. A polymer as claimed in claim 1, which is a copolymer that contains, in addition to units of the formula I containing acid-cleavable groups, units derived from maleimide.

9. A polymer as claimed in claim 1, which is a copolymer that contains, in addition to units of the formula I containing acid-cleavable groups, units derived from methacrylic acid or from an ester or amide of (meth)acrylic acid.

10. A polymer as claimed in claim 11, which is a terpolymer that contains, in addition to two different units of the formula I containing acid-cleavable groups, units derived from methacrylic acid or from an ester or amide of (meth)acrylic acid.

11. A polymer as claimed in claim 1, which is a copolymer that contains, in addition to the units of the formula I containing acid-cleavable groups, units derived from vinyl ether.

12. A polymer as claimed in claim 1, which has a number average molecular weight of about 2,000 to 100,000.

13. A polymer as claimed in claim 12, wherein said molecular weight is between 5,000 and 40,000 g/mol.

14. A polymer as claimed in claim 1, wherein R$^1$ is a tetrahydrofuranyl group.

15. A polymer as claimed in claim 1, wherein R$^1$ is a benzyl group.

16. A polymer as claimed in claim 1, wherein R$^1$ is a trialkylsilyl group.

17. A polymer as claimed in claim 1, wherein R$^1$ is a alkoxycarbonyl group.

18. A polymer as claimed in claim 1, which comprises at least 10 mol% of units of formula (I).

* * * * *